United States Patent [19]

Jessel, Jr. et al.

[11] Plant 4,273

[45] Jun. 27, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 835,830

[22] Filed: Sep. 22, 1977

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Beall & Jeffery

[57] ABSTRACT

A spider capitulum type of chrysanthemum which is a sport of the cultivar Jade, disclosed in pending application Ser. No. 712,192, (now U.S. Plant Pat. No. 4,123) and which is distinguished from the parent cultivar by its medium yellow ray floret color.

1 Drawing Figure

The present invention comprises a new and distinct cultivar of *Chrysanthemum morifolium,* Ramat., hereinafter referred to by the cultivar name Jasmine (#73038A52).

Jasmine is a product of planned sport induction program which had the objective of expanding the color range of the parental cultivar, Jade (#73038052), disclosed in our pending U.S. Plant patent application filed Aug. 6, 1976, Ser. No. 712,192 (now U.S. Plant Pat. No. 4,123).

Jasmine was discovered and selected by William E. Duffett and Walter H. Jessel, Jr. on Aug. 25, 1976 as one plant within a flowering block of Jade in a controlled environment in Barberton, Ohio. Plants within the flowering block were derived from stock plants which had been irradiated as rooted cuttings with an x-ray source of 1800 r units.

The first act of asexual reproduction of Jasmine was accomplished when vegetative cuttings were taken from the initial selection in December, 1976, in a controlled environment in Barberton, Ohio by a technician working under formulations established and supervised by Walter H. Jessel, Jr. and William E. Duffett. Horticultural examination of selected units initiated Aug. 25, 1976 has demonstrated that the combination of characteristics as herein disclosed for Jasmine are firmly fixed and are retained through successive generations of asexual reproduction.

Jasmine has not been observed under all possible environmental conditions. The phenotype may vary significantly with variations in environment such as temperature, light intensity, and day length. The following observations, measurements, and comparisons describe plants grown in Barberton, Ohio under greenhouse environmental conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Jasmine which in combination distinguish this chrysanthemum as a new and distinct cultivar:

1. Flat capitulum form, reflexing slightly at full maturity.
2. Spider capitulum type.
3. Medium yellow ray floret color.

4. Diameter across face of capitulum from 140 to 160 mm. at maturity.
5. Uniform nine week flowering response to photoperiodic short-day control.
6. Medium plant height (requires 1–2 long day weeks prior to pinch and short days and one application 2500 ppm B-9 SP 14 to 21 days after the beginning of short days to attain a flowered plan height of 30 to 45 cm.).
7. Semi-spreading branching pattern.

The accompanying color photographic drawing shows typical inflorescence and foliage characteristics of Jasmine. Color representations are as nearly true as possible with illustrations of this type.

Of the many commercial cultivars known to the present inventors, the most similar existing cultivar in comparison to Jasmine is the parental cultivar, Jade. Reference is made to attached Chart B which compares certain characteristics of Jade with the same characteristics of Jasmine. As noted in Chart B, the primary distinguishing characteristic of Jasmine in comparison to Jade is that of ray floret color. All other characteristics of Jasmine are similar to those same characteristics of Jade.

In the following description, color references are made to The Munsell Limit Color Cascade, 1972 edition. The color values were determined between 8:30 and 9:00 AM on Mar. 21, 1977 under 150 foot-candle light intensity at Barberton, Ohio.

Botanical classification: *Chrysanthemum morifolium,* Ramat., cv Jasmine.

INFLORESCENCE

Capitulum:

*Form.*—Flat, reflexing slightly with age.

*Type.*—Spider.

*Diameter across face.*—140 to 160 mm.

Corolla of ray florets:

*Color (abaxial).*—25-6 to 25-5.

*Color (adaxial).*—26-4 to 26-3.

Reproductive organs:

*Androecium.*—Present disc florets only; scant to numerous; slight pollen.

*Gynoecium.*—Present both ray and disc florets.

PLANT

General appearance: Semi-spreading branching pattern; medium height.

Foliage:

*Color (abaxial).*—Approximately 20-15.

*Color (adaxial).*—Approximately 21-15 overlaid with white.

CHART A

AVERAGE GREENHOUSE CHRYSANTHEMUM ENVIRONMENTS USED FOR BARBERTON, OHIO

| SEASON | TEMPERATURES USED Night | Bright Day | Clouy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7-10 f.c. | To Sept. 15 on - 5:30 PM Off - 7:30 AM | From Oct 15 300 ppm |
| WINTER | 58° F to 62° F | 65° F to 70° F | 60° G to 65° F | 2 to 5 weeks at 5 Hours Per Night of 7-10 f.c. | None | 300 ppm |
| SPRING | 58° F to 65° G | 65° F to 80° F | 60° F to 75° F | 2 to 4 weeks at 5 Hours Per Night of 7-10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7-10 f.c. | On - 6:00 PM Off - 8:00 AM | NONE |

CHART B

COMPARISON OF JASMINE AND JADE

| Cultivar | Ray Floret Color | Diameter Across Face Of Capitulum | Plant Height | Branching Pattern | Flowering Response Period | Capitulum Form and Type |
|---|---|---|---|---|---|---|
| Jasmine | Medium Yellow | 140 to 160 mm. | Medium | Semi-spreading | 9 week | Flat Spider |
| Jade | White | 140 to 165 mm. | Medium | Semi-spreading | 9 week | Flat Spider |

COMPARISONS MADE OF PLANTS GROWN IN A GREENHOUSE IN BARBERTON, OHIO UNDER ENVIRONMENTAL CONDITIONS AS DESCRIBED IN CHART A.

We claim:

1. A new and distinct cultivar of *Chrysanthemum morifolium;* Ramat, known by the cultivar name Jasmine and particularly characterized as to uniqueness by the combined characteristics of flat capitulum form, reflexing slightly with age; spider capitulum type; medium yellow ray floret color; diameter across face of capitulum from 140 to 160 mm. at maturity; uniform 9 week flowering response to photoperiodic short-day control; medium plant height; and semi-spreading branching pattern.

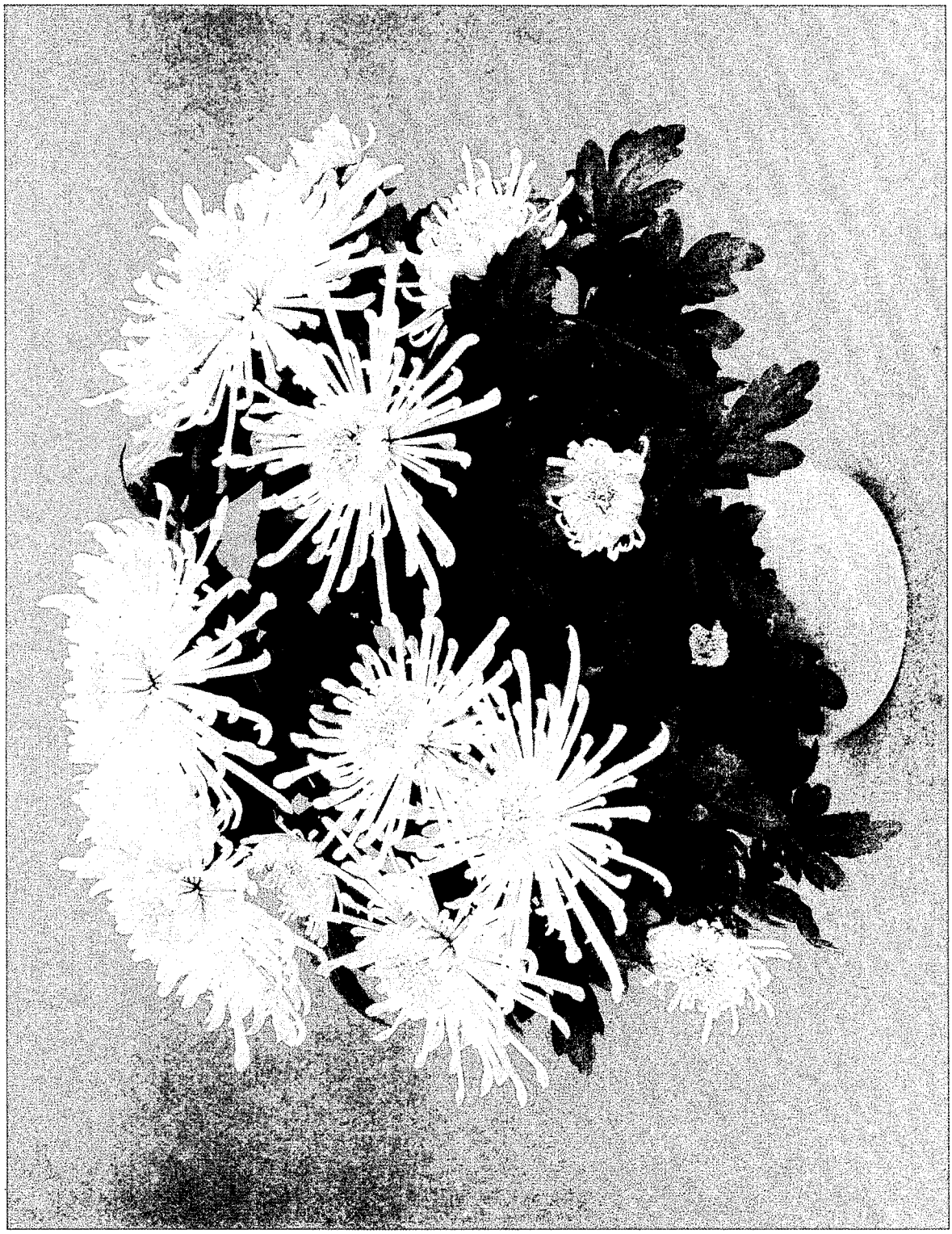

* * * * *